(12) United States Patent
Frank

(10) Patent No.: US 7,032,597 B1
(45) Date of Patent: Apr. 25, 2006

(54) MEDICAL DEVICE FOR OVERCOMING AIRWAY OBSTRUCTION

(76) Inventor: Simon Jacob Frank, 8921 Southern Orchard Rd. North, Davie, FL (US) 33328

( * ) Notice: Subject to any disclaimer, the term of this patent is extended or adjusted under 35 U.S.C. 154(b) by 0 days.

(21) Appl. No.: 11/156,164

(22) Filed: Jun. 17, 2005

(51) Int. Cl.
*A61F 13/00* (2006.01)
(52) U.S. Cl. ........................ 128/846; 128/869
(58) Field of Classification Search ......... 128/846, 128/97.7, 102.1, 103.1, 105.1, 869, 875, 128/870, 876, 878, 879, 207.17; 602/74, 602/36, 17; 297/464, 466, 467
See application file for complete search history.

(56) References Cited

U.S. PATENT DOCUMENTS

| 4,207,881 | A | * | 6/1980 | Richter ..................... 602/17 |
| 5,494,048 | A | | 2/1996 | Carden |
| 5,893,365 | A | * | 4/1999 | Anderson ................ 128/848 |
| 6,196,224 | B1 | | 3/2001 | Alfery |
| 6,200,285 | B1 | | 3/2001 | Towliat |

* cited by examiner

*Primary Examiner*—Henry Bennett
*Assistant Examiner*—Shumaya B. Ali
(74) *Attorney, Agent, or Firm*—Ruben Alcoba, Esq.

(57) ABSTRACT

A medical device for overcoming upper airway obstruction when a patient is placed in a supine position, featuring a harness, a clip that attaches to the harness, and a plate or a bed that receives the clip that is attached to the harness after the medical device is placed on the patient.

20 Claims, 6 Drawing Sheets

MEDICAL DEVICE FOR OVERCOMING AIRWAY OBSTRUCTION

BACKGROUND

Obstruction of the upper airway by the tongue is a common complication when a sedated or unconscious patient is lying in the supine position. The causes of unconsciousness may be sedation, anesthesia, head trauma, drug overdose or any of a multitude of medical causes. The patient may be in any emergency situation. The direct cause is that gravity pulls the person's tongue downwards (towards the cervical spine) and the tongue obstructs the airway and impedes respiration, partially or completely. The airway obstruction discussed above might cause a life-threatening situation if the airway obstruction is not urgently cleared, for hypoxemia and death can quickly ensue.

Anesthesiologists commonly overcome airway obstruction by tilting the patient's head backwards and pulling the chin up towards the ceiling and away from the body (cephalad). Obstruction of the airway is overcome because the base of the tongue is attached to the mandible, and by pulling the chin upward the tongue will be simultaneously pulled upward. This practice is very fatiguing and restricts the anesthesiologist's or emergency responder's ability to perform other functions that require two free hands.

An upper airway can also be maintained open by inserting various medical tubes into the airway, for example, nasal-pharyngeal, oral-pharyngeal, laryngeal mask airway (LMA) and the cuffed oral pharyngeal. But as of today, there are no medical devices in common use that attach externally to the face that will maintain an open upper airway.

In the past, medical personnel have attempted to use surgical tape to attempt to maintain an open upper airway. Anesthesiologist would secure tape around the chin of a patient and then attach the ends of the tape to an operating room table. Tape procedures are unsatisfactory, for the tape attachment pulls back and downwards and do not provide the upward pull required on the chin to maintain an open upper airway. Tape quickly stretches and traction is lost. Tape is not sufficiently adherent to cope with the traction forces and detaches. Other complications with this procedure are skin trauma and eye damage. The tape passes close to the patient's eyes and contact with the eye is unavoidable if the patient coughs or turns the head. The method of attaching tape to the operating room table cannot be used to manage an obstructed airway outside of the operating room, example, at a roadside motor vehicle accident or during subsequent transportation to hospital.

Chin props comprising a ball on the end of an arm secured to the operating room table have also been used to push the chin up. They too have proven to be unsatisfactory and are not commonly used, because they are large and cumbersome and get in the way of surgeons operating on the upper body. Furthermore, if misapplied they may constrict the airway. Chin props with complex mechanisms that attach to suitable operating tables, cannot be used to manage an obstructed airway outside of the operating room, for example, at a roadside motor vehicle accident or during subsequent transportation to hospital.

Information relevant to attempts to address these problems can be found in U.S. Pat. Nos. 5,494,048, 6,200,285 B1, and 6,196,224 B1. However, each one of these references suffers from one or more of the following disadvantages:
1. Can cause eye damage and skin trauma;
2. Require attachment to suitable operating tables;
3. Obstruct the attendant's view of the patient;
4. Do not provide sufficient upward leverage to the chin;
5. Do not lend themselves to use in accident situations;
6. Do not effectively overcome airway obstruction; and
7. Difficulties in removal of devices, should immediate endotracheal intubation be required.

Inside and outside the operating room, an urgent need exists for equipment that overcomes upper airway obstruction and maintains an open upper airway. This equipment should be compatible with and improve the effectiveness of oral-pharyngeal and nasal-pharyngeal airways and face masks. In the operating room, such equipment would allow mask anesthesia to be used for sedated and anesthetized patients instead of general anesthesia and endotracheal intubation with immediate cost savings. Outside the operating room, a need exists for portable, compact equipment that can overcome upper airway obstruction and maintain an open airway and that can be used in cramped quarters such as an ambulance, a hyperbaric chamber and an MRI chamber.

For the foregoing reasons, there is a need for a medical device is safe and reliable that will overcome upper airway obstruction and that will maintain an open airway in the anesthetized and sedated patient lying in a supine position in an operating room and any unconscious patient lying in the supine position at any site. To be effective, the equipment should be safe and easy to use and reliable. The equipment should free up the operators' hands; render oral and nasal pharyngeal airways more effective and not interfere with but facilitate the use of a face mask. The equipment should be free standing, compact and portable.

SUMMARY

The present invention is directed to a medical device that assists in overcoming airway obstruction and maintaining an open airway when a patient, who may or may not be anesthetized, is unconscious and placed in the supine position. This device satisfies the following needs:
1. It frees the practitioner's hands to do other tasks;
2. Does not obstruct the view and allows the practitioner to visually monitor the patient;
3. It is a compact and portable device;
4. It does not cause eye damage or skin trauma;
5. Does not require the use of specific operating room tables when operating the device; and
6. Allows for the easy removal of the device should the patient vomit or emergency endotracheal intubation be required.

The medical device for overcoming airway obstruction comprises of a harness, two clips, and a surface (clip receiving means) to place a patients head when the patient is in the supine position.

The harness comprises of a headband section and of two belt sections. The headband section has front and rear sections. The rear of the headband section has two apertures defined therein. The headband section also has two tightening means. Each belt section has a first and a second end. The first end of each belt section attaches to the front of the headband. The first end of the belt sections is positioned on the headband so that the belts form an X-Junction on the apex of a user's head. The belt sections cross over one another at the apex of a patient's head and are attached to each other at the X-junction. The second end of each belt section inserts through each aperture of the rear section of the headband. The first end of each belt has a VELCRO receiver that is positioned and is attached on the side of each belt section not attached to the headband. Each belt section has a VELCRO attachment means attached to the same side of belt section attached to the headband. The VELCRO attachment means is positioned so that when the harness is placed on the patient, each belt section will pass under the chin of the patient and the VELCRO attachment means will attach to each VELCRO receiver. The second end of each belt section further has a plurality of fenestrations. The term VELCRO when used above and hereinafter in this application shall mean a hook and loop fastener material.

The two clips can be any type of clips that have at least two ends. One end of each clip hooks to the belt at one of the belt's fenestrations. The other end of the clip hooks to the clip receiving means after the patient is placed in a supine position.

The clip receiving means can be a flat plate or a bed.

One of the many advantages of this invention is the simplicity of its construction. The fact that the three main elements of this invention are a harness, a clip and a flat surface, attest to the simplicity of construction of this device.

A further advantage of this invention is that it is a stand-alone medical device. The device does not need to be attached to any supporting devices to become operable. When a patient's head is made to rest on the clip receiving means, after the harness is placed on the patient, and the clips are secured to the harness and to the clip receiving means, the weight of the patient's head on the clip receiving means (when using the plate) is sufficient to secure the medical device so that an upward pull on the chin created by the belts of the harness will be maintained during the use of this device. Remember, as long as this upward pull on the chin is maintained, the upper airway will be maintained open, thus it is key that the tension created with this device not be compromised and this is easily solved by using the weight of the patient's head as the anchor to the device.

Yet another advantage to this invention is that the harness insures that the belts of the harness do not come in contact with the patient's eyes, this is very important for one cannot prevent coughing and other involuntary movements of the head.

DRAWINGS

These and other features, aspects, and advantages of the present invention will become better understood with regard to the following description, appended claims, and drawings where:

DESCRIPTION

Figures 1, 1A:
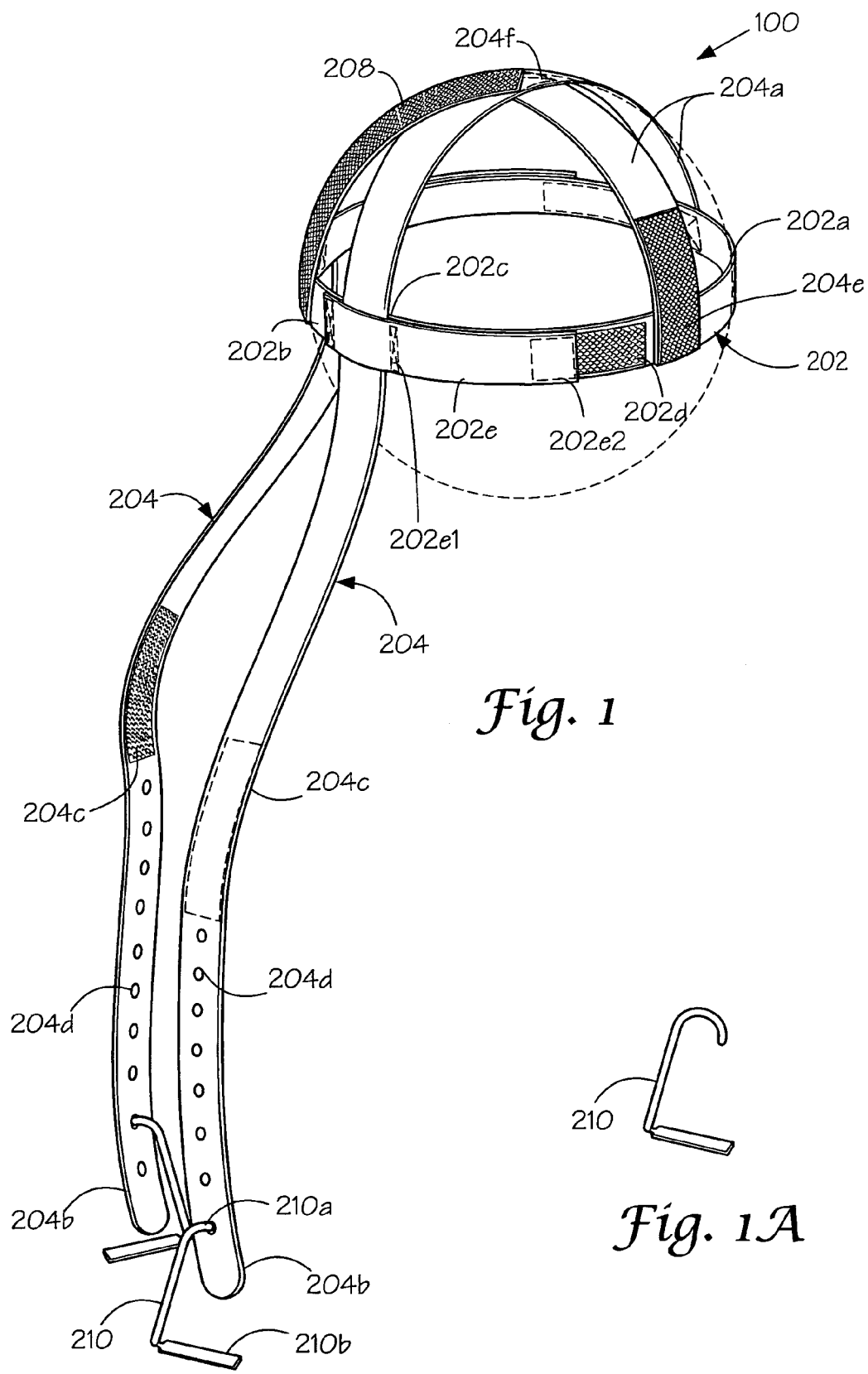
FIG. 1 shows a harness of the medical device of present invention.

As seen in FIGS. 1–4, a medical device used to overcome upper airway obstruction when a patient is placed in a supine position comprises of a harness 100, two clips 210, and a clip receiving means 102/300. The harness 100 comprises a headband section 202, the headband section 202 has a front 202a and a rear 202b section, wherein the rear of the headband 202b has two apertures 202c defined therein, and the headband 202 has two tightening means 202e; and two belt sections 204, each belt section 204 has a first 204a and a second 204b end, the first end of each belt section 204a attaches to the front of the headband 202a, the first end of the belt sections 204a are positioned on the headband 202 so that the belt sections 204 form an X-Junction 204f on the apex of a user's head, the belt sections 204 are crossed over one another and attached to each other at an X-junction 204f and the second end of each belt section 204b inserts through each aperture 202c of the rear section of the headband 202, the first end of each belt 204a section further comprises a VELCRO receiver 204e that is positioned and is attached on the side of each belt section not attached to the headband 202, each belt section 204 has a VELCRO attachment means 204c attached to the same side of belt section attached to the headband location 202d at a position allowing the harness 100 to be placed on a patient and each belt section 204 pass under the chin of the patient and attach to each VELCRO receiver 204e, the second end of each belt section 204b further defining a plurality of fenestrations 204d. The two clips 210 have a first 210a and second end 210b, the first end 210a of each clip attaches to the second end of each belt section 204b at the fenestrations 204d. The clip receiving means 102/300 attaches to the second end of each clip 210b.

The harness 100 is made of any material known in the art of headbands and head medical restraints.

Figure 7:
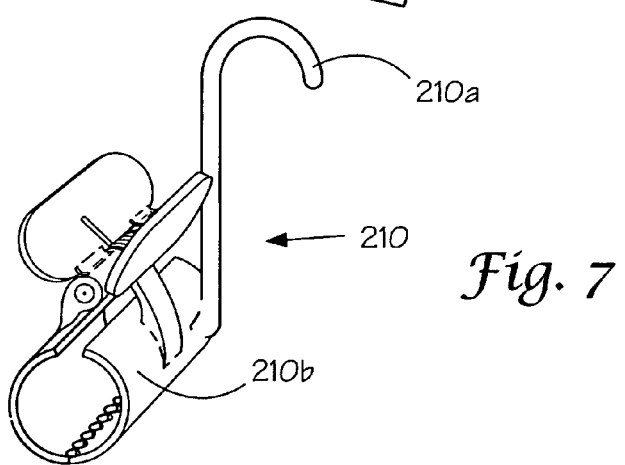
FIG. 7 shows a clip that might be used with the present invention.
Figure 9:
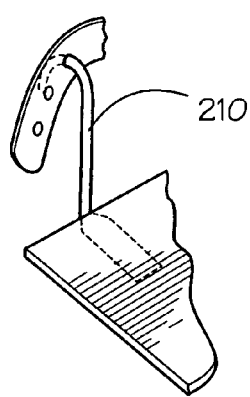
FIG. 9 Shows how the clip attaches to the plate of the present invention.

As seen in FIGS. 1a, 7, and 9, any clip known in the art of clips that has at least two ends can be used with this invention.

Figure 5:
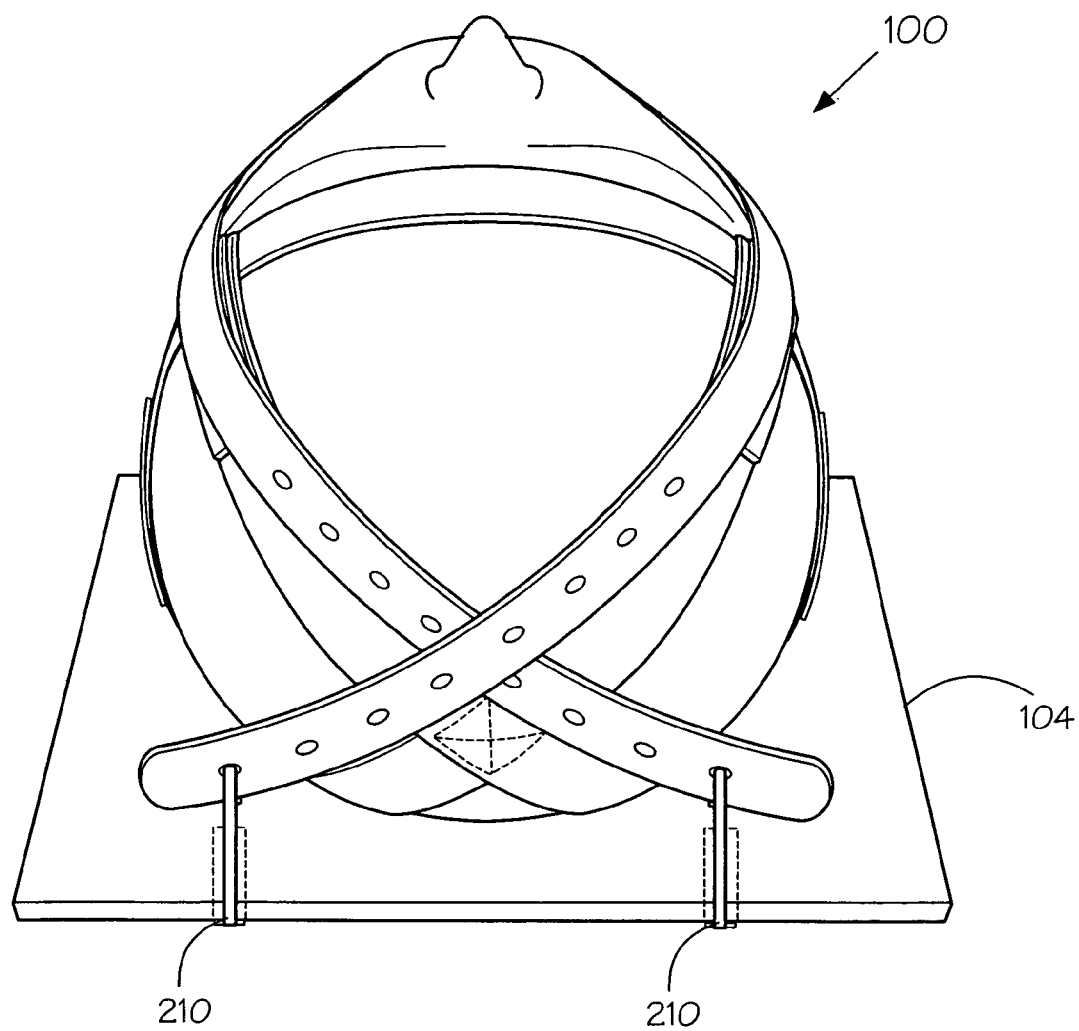
FIG. 5 shows a belt X-junction and how the belts of the present invention are clipped to the invention's clip receiving means.
Figure 6:
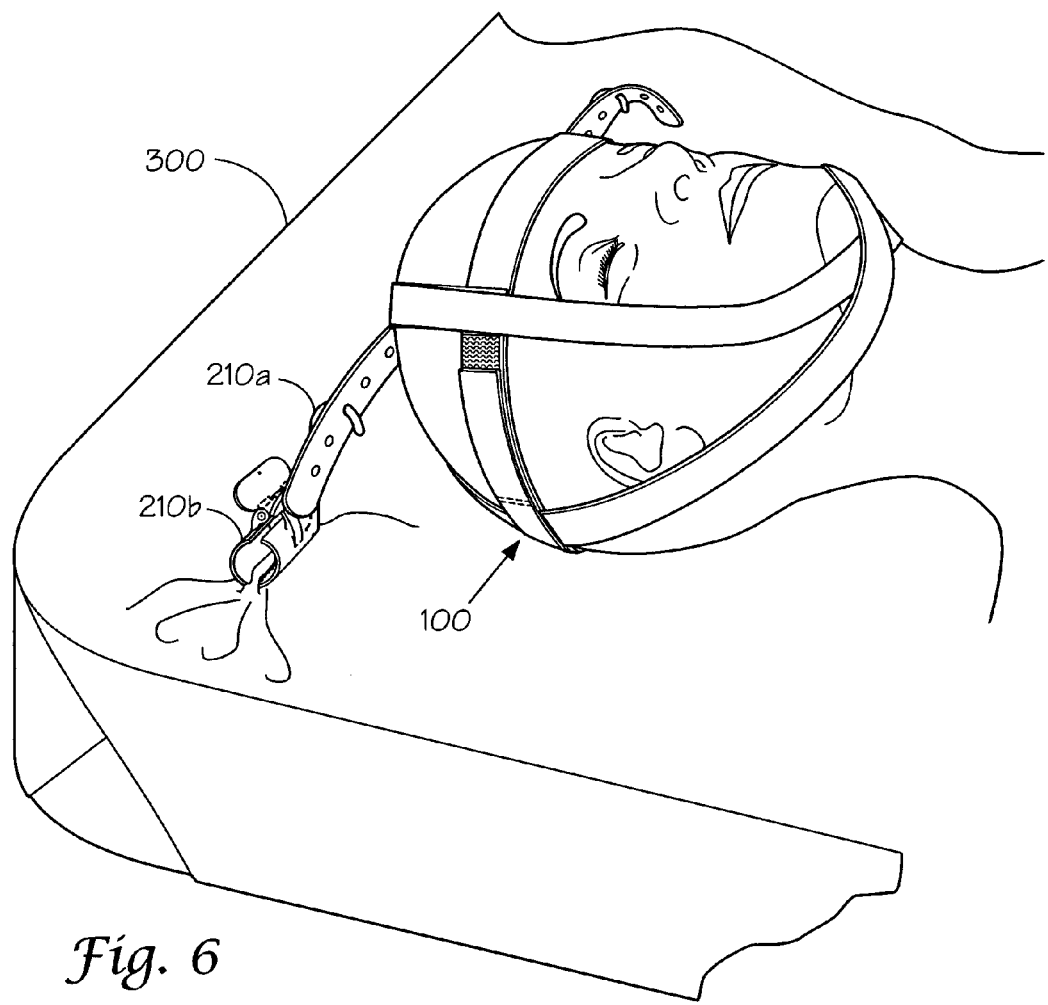
FIG. 6 shows another embodiment of the present invention, this embodiment uses a bed as the clip receiving means.

As seen in FIGS. 5–6, the clip receiving means 102/300 might be a flat plate 102 or a bed 300.

Figure 2:
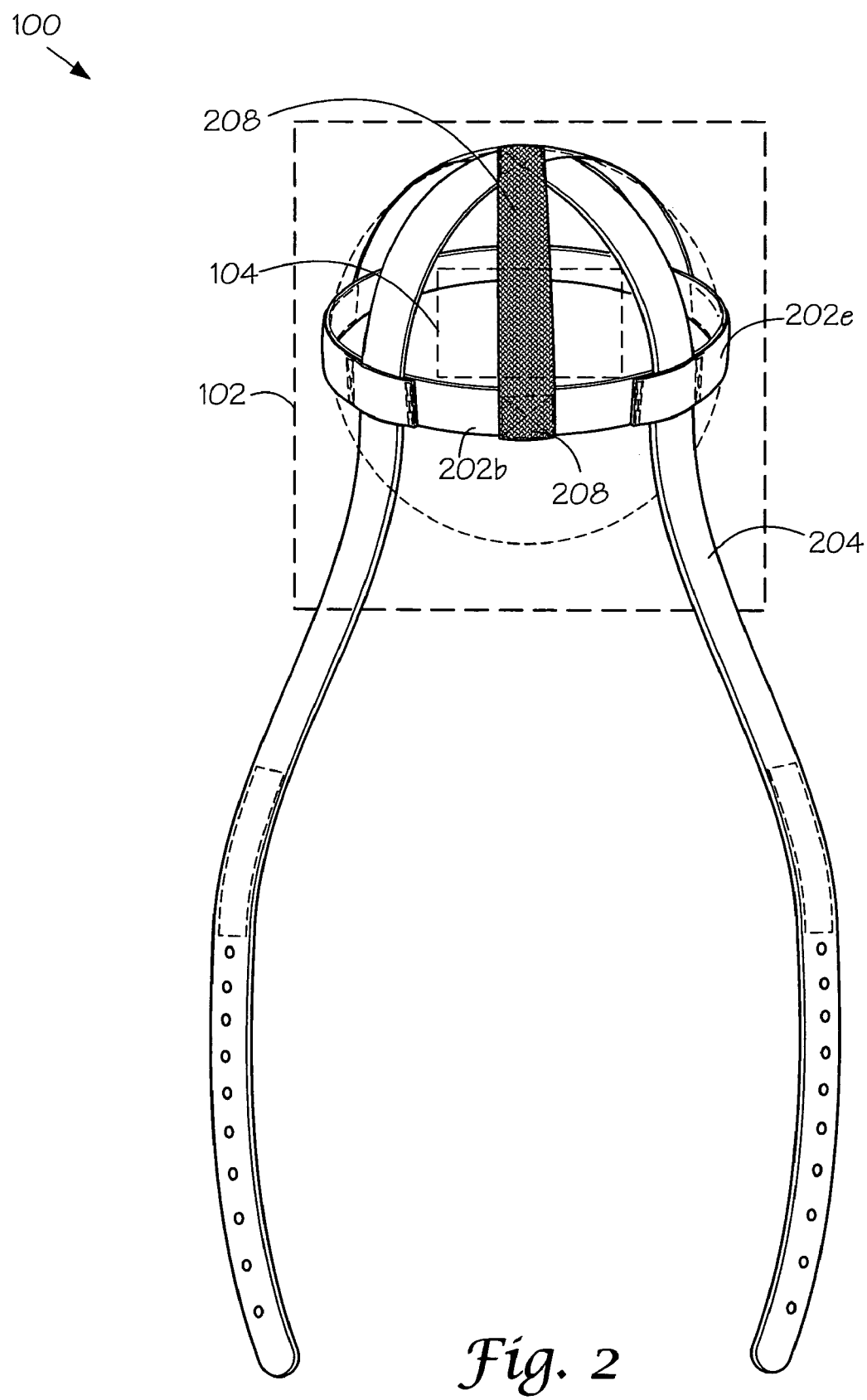
FIG. 2 illustrates the harness and the clip receiving means.
Figure 3:
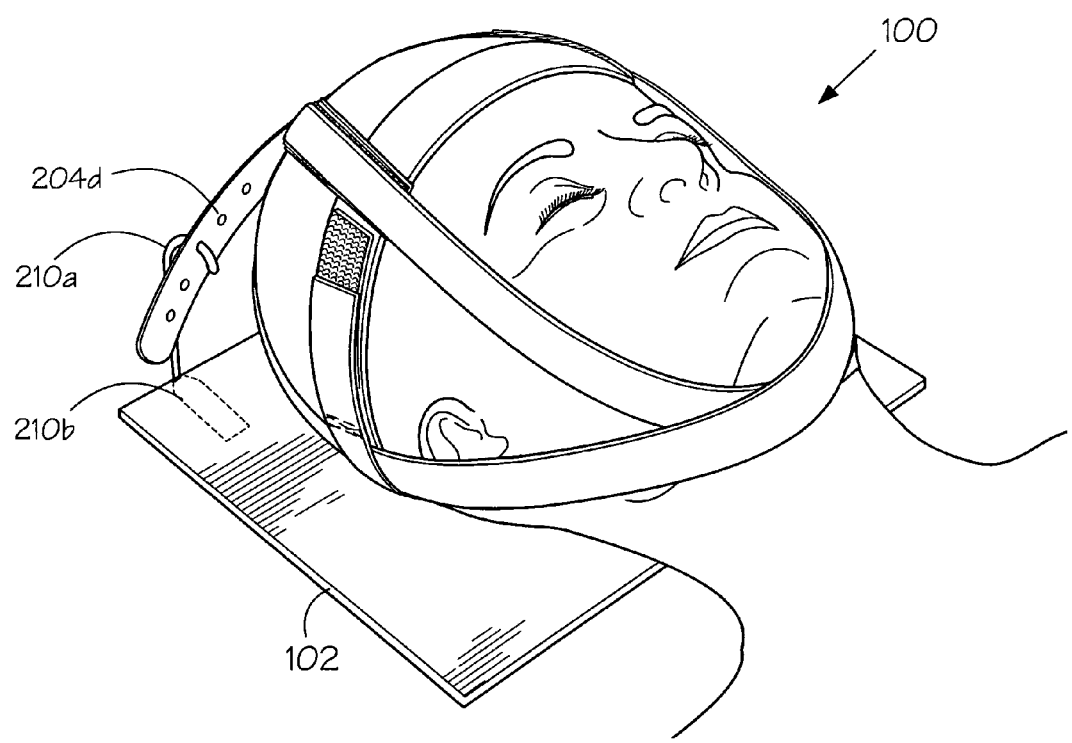
FIG. 3 shows an embodiment of the medical device on a patient.
Figure 4:
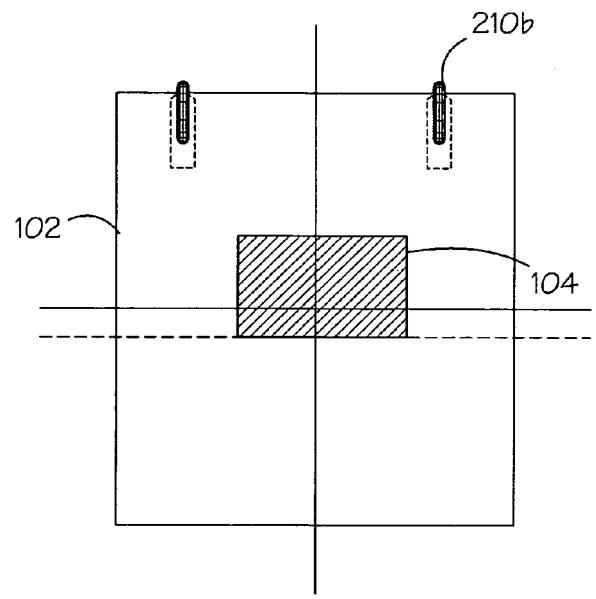
FIG. 4 shows a plate as the clip receiving means of the present invention.

As seen in FIGS. 1, 2, and 4, in a further embodiment of the above invention, the medical device comprises a plate VELCRO receiver 104 and a strip of material 208. The plate Velcro receiver 104 is a material that is attached to the plate 102 that will receive VELCRO. The strip of material 208 has two ends, and one side of the material is VELCRO, wherein one end of the non-VELCRO side of the material attaches to the middle of the rear side of the headband 202b and the other end attaches at the X-junction 204f, the VELCRO side of the strip 208 attaches to the plate VELCRO receiver 104.

As seen in FIGS. 1, 3, 6, and 8, the tightening means 202e of the headband comprises two tension strips attached to the headband 202, each strip 202e having a first 202e1 and a second end 202e2, the first end of each strip 202e1 attached to the headband 202, and the second end of each strip having a strip attachment means 202e2 attachable to the headband location 202d. The strip attachment means 202e2 might be VELCRO.

Figure 8:
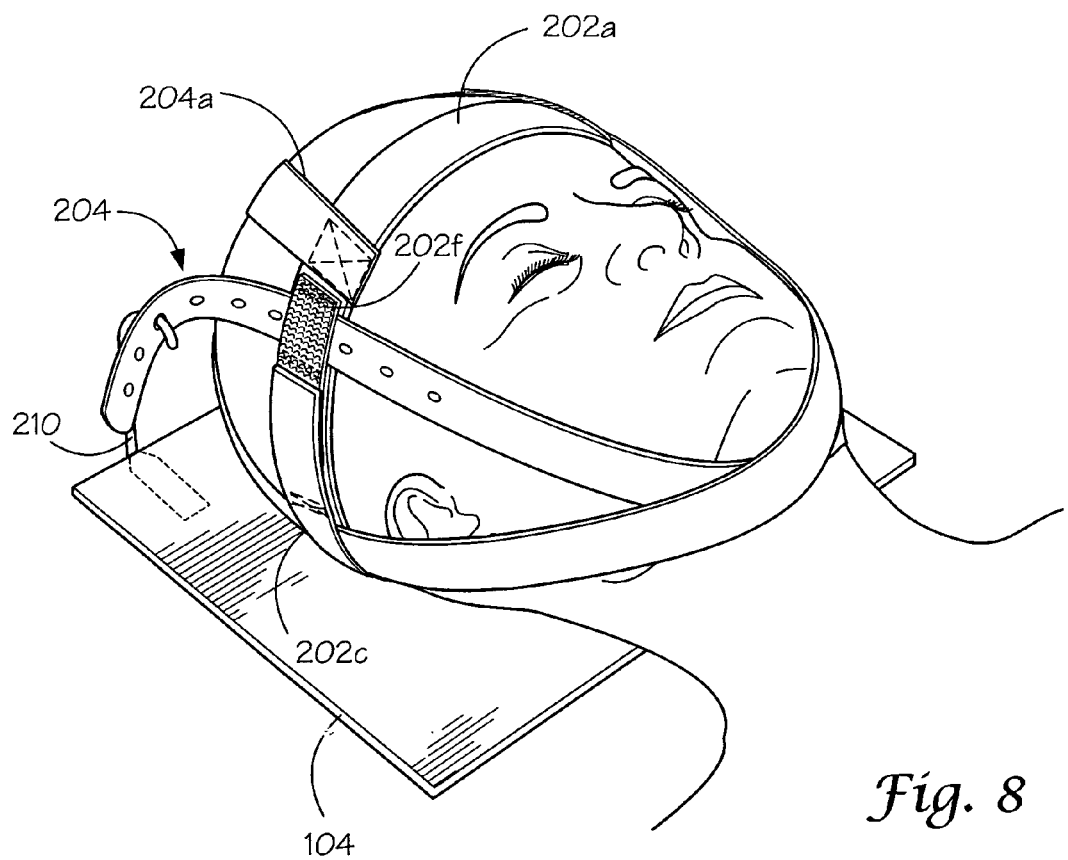
FIG. 8 Shows another variation of the harness of the present invention.

As seen in FIG. 8, in another embodiment of the invention, the harness 100 of the medical device comprises a headband section 202, the headband section 202 has a front 202a and a rear 202b section, wherein the rear of the headband 202b has a first pair of apertures 202c defined therein, the front section 202a has a second pair of apertures 202f defined therein, and the headband 202 has two tightening means 202e; and two belt sections 204, each belt section 204 has a first 204a and a second 204b end, the first end of each belt section 204a attaches to the front of the headband 202a, the first end of the belt sections 204a are positioned on the headband 202 so that the belt sections 204 form an X-Junction 204f on the apex of a user's head, the belt sections 204 cross over one another and attach to each other at the X-junction 204f and the second end of each belt section 204b inserts through each first aperture 202c of the rear section of the headband 202, and the second end of each belt section 204b further inserts through each second aperture 202f after the harness 100 is placed on a patient and each belt section 204 passes under the chin of the patient, the second end 204b of each belt section further defining a plurality of fenestrations 204d. The two clips 210 and the clip receiving means 102/300 are the same as the first embodiment of the medical device recited above.

A method of using the invention in FIGS. 1–7, which comprises the steps of first positioning the clip receiving means on a flat surface, then placing a harness 100 around the head of a patient so that the adjustable ends 204b of the belts of the harness 100 flow from the back of the neck of the patient, next, resting the back of the patients head on the clip receiving means 102, then, threading the belts 204 through the headband's apertures 202c, next pulling the adjustable ends 204b of the belts, then crossing the belts 204 under the lower jaw of the patient so that an upward pull is created on the lower jaw of the patient, next attaching the belt VELCRO attachment means 204c to the belt VELCRO receiver 204e, then crossing the belts 204 at the apex of the patients head, and lastly, securing the clips 210 to the clip receiving means 102/300.

A method of using the invention in FIGS. 8–9, which comprises the steps of first positioning the clip receiving means on a flat surface, then placing a harness 100 around the head of a patient so that the adjustable ends 204b of the belts of the harness 100 flow from the back of the neck of the patient, next, resting the back of the patients head on the clip receiving means 102, then, threading the belts 204 through the headband's first set of apertures 202c, next pulling the adjustable ends 204b of the belts, then crossing the belts 204 under the lower jaw of the patient so that an upward pull is created on the lower jaw of the patient, next threading the belts 204 through the headbands second set of apertures 202f, and lastly, securing the clips 210 to the clip receiving means 102/300.

An advantage of the present invention is that a patient's eyes are never in danger of being damaged, for when the belts are placed to encircle the chin of the patient and then attached to the clip receiving means, the belts are at a position that does not allow the belts to rub against the eyes.

Another advantage of the present invention is a patient can be observed from all positions.

A further advantage of the present invention is that it is compact and rudimentary in its nature.

Yet a further advantage to the device (when using the plate as the clip receiving means) is that it does not require attachment to other structures to become operational, it is an ideal device for practitioners working in the field, paramedics.

Another advantage of the invention is the simplicity in which it can be taken off a patient should an emergency situation arise.

An advantage of this invention is that it promotes sterility, for the harness can be disposable.

Another advantage of this invention is that it is easily stored. The invention is also inexpensive to manufacture, therefore it can be discarded after each use. Discarding the device after each use ensures that the device is sterile when used.

Finally, another advantage of this device is that it frees the hands of the operator, thereby allowing the attendant to treat other problems that the patient might be experiencing and to attend to other patients.

Although the present invention has been described in considerable detail with reference to certain preferred versions thereof, other versions are possible. Therefore the spirit and the scope of the claims should not be limited to the description of the preferred versions contained herein.

What is claimed is:

1. A medical device used to overcome upper airway obstruction when a patient is placed in a supine position comprising:

a harness, the harness comprising;
   a headband section, the headband section having front and rear sections, wherein the rear of the headband has two apertures defined therein, and the headband has two tightening means; and
   two belt sections, each belt section having a first and a second end, the first end of each belt section attached to the front of the headband, the first end of the belt sections are positioned on the headband so that the belt sections form an X-junction on the apex of a user's head, the belt sections are crossed over one another and attached to each other at the X-junction and the second end of each belt section inserts through each aperture of the rear section of the headband, the first end of each belt section further comprising a hook and loop fastener material receiver that is positioned and is attached on a side of each belt section not attached to the headband, each belt section has a hook and loop fastener material attachment means attached to the same side of belt section attached to the headband at a position allowing the harness to be placed on a patient and each belt section pass under the chin of the patient and attach to each hook and loop fastener material receiver, the second end of each belt section further defining a plurality of fenestrations;

two clips, each clip having a first and a second end, the first end of each clip attaches to the second end of each belt section at the fenestrations; and a clip receiving means attached to the second end of each clip.

2. The device of claim 1, wherein the clip receiving means is a flat plate.

3. The device of claim 2, wherein the flat plate further comprises of a plate hook and loop fastener material receiver attached to the plate.

4. The device of claim 3, further comprising a strip of material, the strip of material having two ends, and one side of the material is hook and loop fastener material, wherein one end of the non-hook, and loop fastener material side of the material attaches to the middle of the rear side of the headband and the other end attaches at the X-junction, the hook and loop fastener material side of the strip attaches to the plate hook and loop fastener material receiver.

5. The device of claim 4, wherein the tightening means comprises two tension strips attached to the headband, each strip having a first and a second end, the first end of each strip attached to the headband, and the second end of each strip having a strip attachment means attachable to the headband.

6. The device of claim 5, wherein the strip attachment means is hook and loop fastener material.

7. The device of claim 1, wherein the clip receiving means is a bed.

8. The device of claim 7, wherein the tightening means comprises two tension strips attached to the headband, each strip having a first and a second end, the first end of each strip attached to the headband, and the second end of each strip having a strip attachment means attachable to the headband.

9. The device of claim 8, wherein the strip attachment means is hook and loop fastener material.

10. A medical device used to overcome upper airway obstruction when a patient is placed in a supine position comprising:
   a harness, the harness comprising;
      a headband section having front and rear sections, wherein the rear of the headband has a first pair of apertures defined therein, the front section has a second pair of apertures defined therein, and the headband has two tightening means;
      two belt sections, each belt section having a first and a second end, the first end of each belt section attached to the front of the headband, the first end of the belt sections are positioned on the headband so that the belt sections form an X-junction on the apex of a user's head, the belt sections are crossed over one another and attached to each other at the X-junction and the second end of each belt section inserts through each first aperture of the rear section of the headband, and the second end of each belt section further inserts through each second aperture after the harness is placed on a patient and each belt section passes under the chin of the patient, the second end of each belt section further defining a plurality of fenestrations;
   two clips, each clip having a first and a second end, the first end of each clip attached to the second end of each belt section at the fenestrations; and
   a clip receiving means attached to the second end of each clip.

11. The device of claim 10, wherein the clip receiving means is a flat plate.

12. The device of claim 11, wherein the flat plate further comprises a plate hook and loop fastener ma receiver attached to the plate.

13. The device of claim 12, further comprising a strip of material, the strip of material having two ends, and one side of the material is hook and loop fastener material, wherein one end of the non-hook and loop fastener material side of the material attaches to the middle of the rear side of the headband and the other end is attached at the X-junction, the hook and loop fastener material side of the strip attached to the plate hook and loop fastener material receiver.

14. The device of claim 13, wherein the tightening means comprises two tension strips attached to the headband, each tension having a first and a second end, the first end of each strip attached to the headband, and the second end of each strip having a strip attachment means that attachable to the headband.

15. The device of claim 14, wherein the strip attachment means is hook and loop fastener material.

16. The device of claim 10, wherein the clip receiving means is a bed.

17. The device of claim 16, wherein the tightening means comprises of two tension strips attached to the headband, each strip having a first and a second ends, the first end of each strip attached to the headband, and the second end of each strip having a strip attachment means attachable to the headband.

18. The device of claim 17, wherein the strip attachment means is hook and loop fastener material.

19. A method of using the device of claim 1, comprising the steps of:
   first, positioning the clip receiving means on a flat surface;
   then, placing a harness around the head of a patient so that the adjustable ends of the belts of the harness flow from the back of the neck of the patient;
   next, resting the back of the patients head on the clip receiving means;
   then, threading the belts through the headband's apertures;
   next, pulling the adjustable ends of the belts;
   then crossing the belts under the lower jaw of the patient so that an upward pull is created on the lower jaw of the patient;
   next attaching the belt hook and loop fastener material attachment means to the belt hook and loop fastener material receiver;
   then crossing the belts at the apex of the patients head; and
   lastly, securing the clips to the clip receiving means.

20. A method of using the device of claim 10, comprising the steps of:
   first, positioning the clip receiving means on a flat surface;
   then, placing a harness around the head of a patient so that the adjustable ends of the belts of the harness flow from the back of the neck of the patient;
   next, resting the back of the patients head on the clip receiving means;
   then, threading the belts through the headband's first set of apertures;
   next, pulling the adjustable ends of the belts;
   then, crossing the belts under the lower jaw of the patient so that an upward pull is created on the lower jaw of the patient;
   next threading the belts through the headbands second set of apertures; and
   lastly, securing the clips to the clip receiving means.

* * * * *